United States Patent [19]
Douglas et al.

[11] Patent Number: 5,989,845
[45] Date of Patent: Nov. 23, 1999

[54] DIAGNOSTIC COMPOSITIONS AND DEVICES UTILIZING SAME

[75] Inventors: Joel S. Douglas, Santa Clara; Karen R. Drexler, Los Altos Hills, both of Calif.

[73] Assignee: Mercury Diagnostics, Inc., Scotts Valley, Calif.

[21] Appl. No.: 09/151,096

[22] Filed: Sep. 10, 1998

Related U.S. Application Data

[63] Continuation-in-part of application No. 09/037,653, Mar. 10, 1998, Pat. No. 5,885,790, which is a continuation of application No. 08/628,794, Apr. 5, 1996, Pat. No. 5,776,719.

[51] Int. Cl.$^6$ .................................................... C12Q 1/26
[52] U.S. Cl. .................................................... 435/25
[58] Field of Search ........................... 435/25, 28, 14, 435/4, 18, 808, 814, 970; 564/305, 250; 562/89, 493; 544/49

[56] References Cited

U.S. PATENT DOCUMENTS

| | | | |
|---|---|---|---|
| 3,964,871 | 6/1976 | Hochstrasser | 435/28 |
| 4,059,407 | 11/1977 | Hochstrasser | 435/28 |
| 4,101,381 | 7/1978 | Klose et al. | 435/28 |
| 4,168,205 | 9/1979 | Danninger et al. | 435/28 |
| 4,247,297 | 1/1981 | Berti et al. | 435/28 |
| 4,247,631 | 1/1981 | Nix et al. | 435/28 |
| 4,260,679 | 4/1981 | Tsuda et al. | 435/28 |
| 4,278,439 | 7/1981 | White | 435/28 |
| 4,367,285 | 1/1983 | Yamaguchi et al. | 435/28 |
| 4,385,114 | 5/1983 | Güthlein et al. | 435/28 |
| 4,416,983 | 11/1983 | Röder et al. | 435/28 |
| 4,492,754 | 1/1985 | Trager et al. | 435/28 |
| 4,605,629 | 8/1986 | Lange et al. | 435/28 |
| 4,734,360 | 3/1988 | Philips et al. | 435/28 |
| 4,820,632 | 4/1989 | Frey et al. | 435/28 |
| 4,851,335 | 7/1989 | Kerscher et al. | 435/28 |
| 5,059,394 | 10/1991 | Phillips et al. | 435/28 |
| 5,082,626 | 1/1992 | Grage, Jr. | 435/28 |
| 5,084,382 | 1/1992 | Frey et al. | 435/28 |
| 5,304,468 | 4/1994 | Phillips et al. | 435/28 |
| 5,306,623 | 4/1994 | Kiser | 435/28 |
| 5,315,035 | 5/1994 | Frey et al. | 435/28 |
| 5,334,508 | 8/1994 | Hoenes | 435/28 |
| 5,453,360 | 9/1995 | Yu | 435/28 |
| 5,526,120 | 6/1996 | Jina et al. | 435/28 |
| 5,563,031 | 10/1996 | Yu | 435/28 |
| 5,776,719 | 7/1998 | Douglas et al. | 435/28 |
| 5,885,790 | 3/1999 | Douglas et al. | 435/28 |

FOREIGN PATENT DOCUMENTS

| | | | |
|---|---|---|---|
| 0 007 787 | 2/1980 | European Pat. Off. | 435/28 |
| 328 029 | 8/1989 | European Pat. Off. | 435/28 |
| 0 735 369 | 10/1996 | European Pat. Off. | 435/28 |
| 43 43 082 A1 | 6/1995 | Germany | 435/28 |
| 07311498 | 2/1995 | Japan | 435/28 |
| 938029 | 9/1963 | United Kingdom | 435/28 |
| 90/90/06372 | 6/1990 | WIPO | 435/28 |

OTHER PUBLICATIONS

*Chemical Abstract*, 95:38761 (1981)., Month not available.
M. Mizoguchi, et al., Bunseki Kagaku, 45(2): 111–124 (1996) (and an English language abstract). Month not available.
International Search Report, PCT/US97/1177, International Filing Date Jul. 7, 1997, mailed Nov. 12, 1997.

*Primary Examiner*—Louise N. Leary
*Attorney, Agent, or Firm*—Burns, Doane, Swecker & Mathis LLP

[57] ABSTRACT

A dry chemistry reagent matrix composition is provided containing a matrix material and a reagent composition containing 3-methyl-6-(sulfonate salt)-benzothiazolinone-(2)-hydrazone (MBTH-S), N-ethyl-N-(3-sulfopropyl) aniline, and an oxidase enzyme or a peroxidase enzyme or a mixture thereof. The dry chemistry reagent matrix composition is useful in reagent test strips for determining the presence or concentration of an analyte in a fluid sample, such as blood.

21 Claims, 2 Drawing Sheets

DIAGNOSTIC COMPOSITIONS AND DEVICES UTILIZING SAME

CROSS-REFERENCE TO RELATED APPLICATIONS

This application is a continuation-in-part (CIP) of U.S. Ser. No. 09/037,653, filed Mar. 10, 1998, now U.S. Pat. No. 5,885,790 which application is a continuation of U.S. Ser. No. 08/628,794, filed Apr. 5, 1996, now U.S. Pat. No. 5,776,719. These patent applications are incorporated herein by reference in their entirety.

BACKGROUND OF THE INVENTION

1. Field of the Invention

The present invention relates to dye compositions used for colorimetric determination of a chemical or biochemical component (analyte) in an aqueous fluid, such as blood. In particular, the present invention relates to the field of dry reagent matrix compositions for use on test strips adapted to receive a liquid sample of body fluid whereby a dye indicator composition wetted by the fluid reacts with an analyte in the body fluid and provides a visual or color indication of the presence or concentration of the analyte.

2. State of the Art

Indicator compositions for use in devices for color indication of various analytes in liquid samples, such as body fluids, are well known in the art and are embodied in numerous commercial products, such as dry reagent test strips. In such test strips, a dye or dye couple composition is typically formulated in a solution which is applied to a test strip matrix and then dried to form a dry chemistry reagent system on the test strip. The dry chemistry reagent system commonly involves an oxidizable dye or dye couple composition in combination with a oxidase or peroxidase specific for the analyte to be tested. When the dry chemistry reagent system is contacted with a liquid sample containing the analyte, the analyte reacts with its corresponding oxidase or peroxidase producing hydrogen peroxide which in turn oxidizes the dye or dye couple to produce the desired color change thereby indicating the presence or concentration of the analyte.

Example of such dry chemistry reagent systems are disclosed by Phillips et al. in U.S. Pat. Nos. 4,734,360; 5,059,394 and 5,304,468; by Yu in U.S. Pat. No. 5,453,360; Hoenes in U.S. Pat. No. 5,334,508 and by Hochstrasser in U.S. Pat. Nos. 3,964,871 and 4,059,407. The disclosures of these patents are incorporated herein by reference in their entirety.

A number of dry chemistry reagent systems have been incorporated into various commercial products. While such products generally provide acceptable indication and testing under some conditions, certain problems exist with prior dry chemistry systems. For example, in some dry chemistry reagent systems, the dye components tend to sublime over time from the test strip so that when the test strip is used by the consumer it may not provide an accurate indication. This problem limits the shelf life of the test strips.

Additionally, in some dry chemistry reagent systems, the color change provided by the dye or dye couple components continues to change over time rather than reaching a stable end point. When such dye systems are employed, the color indication must be accurately read at specific time intervals in order to obtain an accurate indication of the presence or concentration of an analyte.

Moreover, some dry chemistry reagent systems require a low pH to provide the necessary stability for the dye or dye couple system. However, the pH of such systems is often below the desired pH level for stability of the enzyme used in the dry chemistry system. Therefore, the amount of enzyme employed in the formulation must be increased to compensate for the enzyme's instability, thus increasing the cost of the dry chemistry reagent system. Additionally, when the enzyme is used under non-optimal pH conditions, the enzyme may give undesired or false indications of the presence or concentration of the analyte.

Finally, in some dye or dye couple systems, the optimum wavelength for determining the presence or concentration of an analyte is often obscured or interfered with by components of the body fluid being analyzed, such as hemoglobin.

In view of the above, it is an object of this invention to provide a dry chemistry reagent system having improved stability regarding sublimation of the dye or dye couple system from the dry chemistry test strips.

It is also an object of this invention to provide a dry chemistry reagent system which rapidly produces a stable end point in a short period of time thus eliminating the time dependent measurements or determinations by the user.

It is a further object of this invention to provide a dry chemistry reagent system which can be formulated and used at a pH range more closely approximating physiological pH thus providing a more stable system for the enzyme or enzymes employed in the manufacture and use of the dry chemistry system.

It is a still further object of this invention to provide a dry chemistry reagent system which permits an accurate determination of the presence or concentration of an analyte in a body fluid without significant spectral interference by components of the body fluid being tested.

The above objects as well as others are achieved by the compositions, devices and methods of this invention as disclosed herein.

SUMMARY OF THE INVENTION

The present invention provides dry chemistry reagent matrix composition comprising a matrix material and a reagent composition comprising 3-methyl-6-(sulfonate salts)-benzothiazolinone-(2)-hydrazone (MBTH-S), N-ethyl-N-(3-sulfopropyl)aniline (ALPS), and an oxidase and/or a peroxidase enzyme, wherein the reagent composition has been imbibed and dried into or onto the matrix material. This invention is also directed to devices containing such dry chemistry reagent matrix compositions and to methods for determining the presence or concentration of analytes in a fluid sample, such as blood, using the compositions and devices described herein.

Among other factors, the present invention is based on the surprising and unexpected discovery that a dry chemistry reagent system comprising MBTH-S, ALPS and an oxidase enzyme and/or peroxidase enzyme permits the determination of the presence or concentration of an analyte in blood without spectral interference from hemoglobin, i.e., it has improved hematocrit performance. Additionally, this dry chemistry reagent system has a stable end point and may be formulated at a pH range of about 6. Moreover, in another embodiment of this invention, it has been discovered that a dry chemistry reagent system comprising MBTH-S, ALPS, N-(3-sulfopropyl)aniline (HALPS) and an oxidase enzyme and/or peroxidase enzyme has improved dry chemistry stability compared to a dry chemistry system comprising MBTH-S, HALPS and an oxidase enzyme and/or peroxidase enzyme.

Accordingly, in one of its composition aspects, the present invention is directed to a dry chemistry reagent matrix composition comprising a matrix material and a reagent composition comprising 3-methyl-6(M sulfonate)-benzothiazolinone-(2)-hydrazone (MBTH-S) where M is a positive ion providing a stable sulfonate salt; N-ethyl-N-(3-sulfopropyl)aniline or a salt thereof; and an oxidase enzyme or a peroxidase enzyme or mixture thereof, wherein the reagent composition has been imbibed and dried into or onto the matrix material.

Optionally, the reagent composition further comprises a third dye component selected from the group consisting of 3,3-dimethylaminobenzoic acid, 3,5-dichloro-2-hydroxybenzenesulfonic acid, 8-anilino-1-naphthelenesulfonate, N-(3-sulfopropyl)aniline or salts thereof. Preferably, the third dye component is N-(3-sulfopropyl)aniline (HALPS) or a salt thereof.

The dry chemistry reagent composition may further comprise conventional binders, chelating agents, buffers and the like. Such components are well known in the art. The dry chemistry reagent composition is imbibed and dried into or onto a matrix material (i.e., a filter material), such as Gelman Sciences polyethersulfone membrane. The matrix material provides a carrier system for the reagent composition.

The MBTH-S is used in the composition in form of a stable sulfonate salt, of which the sodium salt is preferred, but the potassium, ammonium or other ionic form of the sulfonate salt may be used. In this invention, the MBTH-S is used with ALPS to form a dye couple having improved indication properties. Preferably, the dye composition is used at a physiological pH, more preferably at a pH in the range of about 6 to 8, still more preferably at a pH of about 6.

In another of its composition aspects, the present invention is directed to a device for testing a fluid for the presence or concentration of an analyte comprising:

a support member comprising a matrix material;

a dry chemistry reagent composition positioned on or impregnated in said support member, said reagent composition comprising 3-methyl-6(M sulfonate)-benzothiazolinone-(2)-hydrazone (MBTH-S) where M is a positive ion providing a stable sulfonate salt; N-ethyl-N-(3-sulfopropyl)aniline or a salt thereof; and an oxidase enzyme or a peroxidase enzyme or a mixture thereof;

whereby the support member is adapted for receiving a fluid sample which contacts said reagent composition and adapted for the support member to provide for inspection or reading of the color change produced by said reagent composition after contact with the fluid sample.

The various mechanical configurations of such devices are known in the art and various configurations may be used incorporating the dry chemistry reagent system of this invention adapted as desired for the particular testing to be accomplished.

This invention also provides methods for determining the presence or concentration of analytes in an aqueous solution, such as blood, using the compositions and devices described herein.

Accordingly, in one of its method aspects, this invention provides a method of testing a fluid for the presence or concentration of an analyte, comprising:

applying a fluid sample to a support member comprising a matrix material having positioned thereon or impregnated therein a dry chemistry reagent composition comprising 3-methyl-6(M sulfonate)-benzothiazolinone-(2)hydrazone (MBTH-S) where M is a positive ion providing a stable sulfonate salt; N-ethyl-N-(3-sulfopropyl)aniline or a salt thereof; and an oxidase enzyme or a peroxidase enzyme or a mixture thereof; whereby the support member is adapted for receiving a fluid sample which contacts said reagent composition and adapted for the support member to provide for inspection or reading of the color change produced by said reagent composition after contact with the fluid sample; and reading or measuring the color indication provided by said reagent composition after contact with said fluid sample.

DETAILED DESCRIPTION OF THE INVENTION

Figure 1:
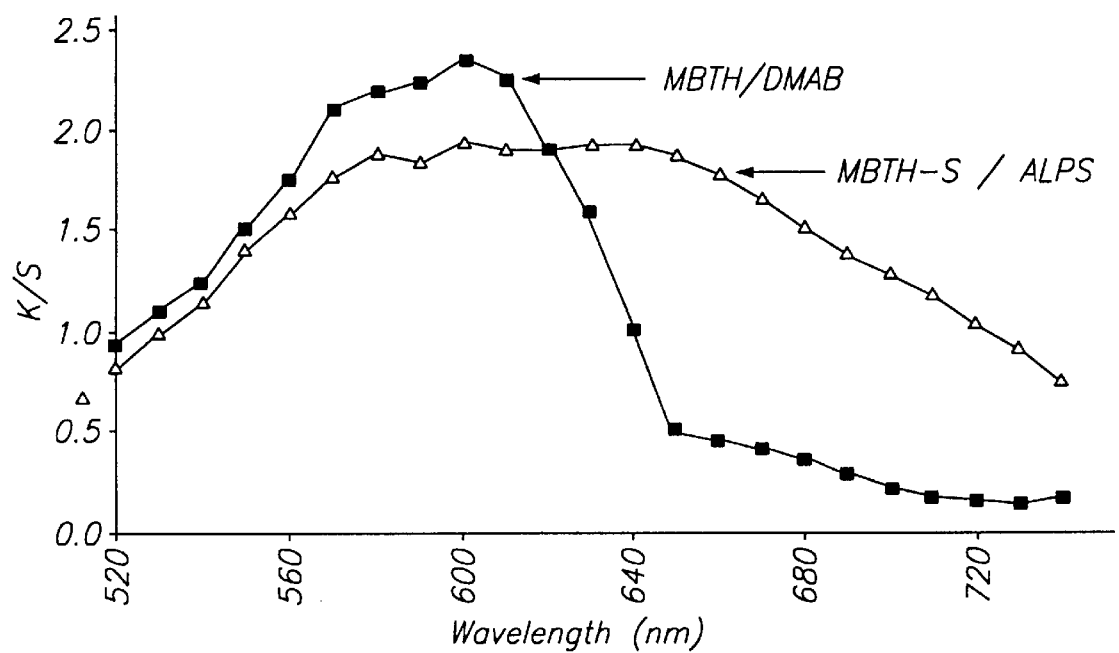
FIG. 1 shows a comparison of the reflectance at certain light wavelengths of dye systems based on (MBTH-S)-ALPS and based on MBTH-DMAB.

Dry chemistry indicator systems for use in test strips, such as those used for testing for glucose in blood, are well known in the art. Therefore, this disclosure is directed to one skilled in the art having knowledge of how to formulate a dye or dye couple composition into a dry chemistry reagent system on a test strip. The test strip typically is in the form of an absorbent matrix adapted for containing the dry chemistry reagent indication system and for receiving the fluid sample to react with the dry chemistry reagent indicator system. A suitable matrix is Gelman Sciences 200D polyethersulfone membrane.

Among other factors, this invention provides an improved dye indicator system based on the use of 3-methyl-6-(M sulfonate)-benzothiazolinone-(2)-hydrazone (MBTH-S), wherein M is a positive ion providing a stable sulfonate sale, preferably sodium, potassium, ammonium or other equivalent ion. Dry chemistry reagent dye systems comprising MBTH-S provide a dry chemistry system on test strips which are resistant to sublimation of the dye in the dry chemistry system and thus provide extended shelf life and increased reliability of the test strips containing the MBTH-S dye system. In addition, dry chemistry reagent dye systems formulated based on the MBTH-S of this invention can be formulated and buffered to operate in a pH range of about 6, which provides additional stability of the oxidase enzymes or peroxidase enzymes present in the dye indicator system. In addition, the dry chemistry reagent dye systems formulated based on the MBTH-S of this invention also provide a stable color reaction end point which is reached in a short period of time after applying the fluid sample. This enables the user to read and interpret the color indication without dependence on accurate timing or taking readings at specific time intervals, which usually requires the use of an electronic meter for accurate measurement and timing. This end point stability of the dye system of this invention also enables the use of the test strip as at least a semi-permanent record of the test results.

The dye systems of this invention are useful in a variety devices and systems including those involving the reaction of whole blood or other unfiltered fluid with the dry chemistry reagent dye system. In such devices and systems, the color presence of whole blood obscures to visual inspection the indicator color change, but these systems can be read and measured by reflectance at certain specific light wavelengths by an appropriate electronic meter system. The dye systems according to this invention are particularly useful in devices and systems that separate the blood solids such as red blood cells from blood fluids and allow the clear blood fluids to contact and react with the dry chemistry reagent dye system, thus providing an unobscured, visually readable color change. In particular the dye system of the present invention is useful in the devices and systems disclosed in co-pending application Ser. No. 08/628,489 (Attorney Docket No. 018176-002) filed Apr. 5, 1996, which disclosure is incorporated herein by reference in its entirety.

In general, it will be recognized by those skilled in the art that the MBTH-S dye system of this invention can be formulated and implemented in many of the dye systems previously based on MBTH by making the appropriate adjustment in buffer and other components to accommodate the different pH range and other properties of MBTH-S compared to the conventional MBTH.

The dry chemistry reagent system of this invention is formulated to enable to analyte to react with a specific oxidase enzyme to produce hydrogen peroxide which reacts with the MBTH-S based-indicator system according to this invention to produce a color change which is visually read or electronically measured with a meter. The oxidase enzyme may be selected from glucose oxidase, cholesterol oxidase, uricase, alcohol oxidase, aldehyde oxidase, glycerophosphate oxidase or other similar oxidase enzymes known in the art to be particularly reactive with a particular analyte. The system may also include the presence of a peroxidase enzyme such as horseradish peroxidase or other known peroxidase to produce or enhance the desired color change in the indicator. The indicator reagent dye system is formulated in a solution and is typically impregnated into a porous matrix or membrane such as a polyethersulfone membrane available from Gelman Science, Ann Arbor, Mich., or a fiberglass matrix available from AhlstromFiltration, Inc., Chatanooga, Tenn., and dried to provide a dry chemistry system useful in the conventional test strips. The MBTH-S-based dye system employed in this invention comprises MBTH-S, N-ethyl-N-(3-sulfopropyl) aniline (ALPS), and optionally a third dye component selected from the group consisting of 3,3-dimethylaminobenzoic acid (DMAB), 3,5-dichloro-2-hydroxybenzene-sulfonic acid (DCHBS),8-anilino-1-naphthalenesulfonate (ANS), or N-(3-sulfopropyl)aniline (HALPS). Other dye compounds which provide a sufficiently high extinction point (approx. 7.0 or higher is preferred) and which form an appropriate dye couple with MBTH-S can be used in the dye system of this invention. Formulation thereof will be apparent to one skilled in the art following the teachings herein. Reference is made to the Reagents Catalog from Dojindo Laboratories, Tokyo, Japan, and to a paper enetitled "Reagents Used for Detecting Substances in Biological Matrix by Enzymatic Methods" published by Dojindo Laboratories at a 1995 Pacific Rim Conference, for other dyes of appropriate properties for use in this invention.

By using MBTH-S and ALPS, a dye composition is provided which can be used at physiological pH, preferably about pH 6, thereby permitting fluid samples to be tested in this pH range. Moreover, this dye composition has stable end point chemistry and is water soluble and does not sublime over time when applied and dried in the membrane matrix. Furthermore, the MBTH-S coupled with ALPS provides flat spectral absorption in the region of about 580 to 680 nm. Moreover, at 654 nm, this system shows a good end point and minimal hematocrit interference.

It will be apparent to one skilled in the art that the selection of the additional dye components to be combined with the MBTH-S and ALPS or to provide dye couple systems with MBTH-S and ALPS will depend on the analyte to be detected, the conditions under which the test strip is to be stored and used and other conventional considerations. However it has been found that the dye couple formed from the combination of MBTH-S and ALPS provides a preferred dye couple system, particularly for formulation with glucose oxidase for glucose detection and measurement in blood fluids. ALPS can also be used to improve other systems, for example, the addition of ALPS to MBTH-S/HALPS has been found to improve the stability of that system.

The preparation of 3-methyl-6-(M sulfonate)-benzothiazolinone-(2)-hydrazone (MBTH-S) is disclosed in U.S. Pat. No. 4,101,381, issued Jul. 18, 1978, the disclosure of which is incorporated herein by reference in its entirety. The preferred MBTH-S is where M is Na. The preferred sodium sulfonate salt is prepared as follows: 85 grams of 3-methyl-benzothiazolinone-(2)-hydrazone (MBTH, available from Aldrich Chemical Co., Milwaukee, Wis., USA) is dissolved in 750 grams of 25% oleum situated in an ice bath so that the temperature is not allowed to exceed 30° C. Upon standing at room temperature for 12 hours complete solution is obtained. The solution is poured into 8 liters of 0° C. water containing excess ice to maintain the 0° C. temperature. Upon standing for about 8 hours the free sulfonic acid precipitate is filtered out, washed and dried. Approximately 85 grams of crude product is obtained, which is purified by repeat extractions with boiling methanol. The resulting solid is washed with water and dissolved in an equimolar amount of 3N NaOH with heating. This solution is filtered over activated charcoal and treated with a double volume of dioxane then allowed to crystallize overnight at about 5° C. The product is then subjected to repeated recrystallizations from 10% NaAcetate with concurrent activated charcoal filtration until the material is almost white. The final material is recrystallized from water and washed with 70% dioxane, then with pure dioxane, then with ether. The resulting crystals of 3-methyl-6-(sodium sulfonate)-benzothiazolinone-(2)-hydrazone are air dried.

N-ethyl-N-(3-sulfopropyl)aniline (ALPS) is commercially available from Dojindo Laboratories, Kumamoto, Japan.

Typically, the dry chemistry reagent system of this invention will comprise from about 5 to about 50% by weight of MBTH-S; from about 5 to about 50% by weight of ALPS; and from about 5 to about 50% by weight of an oxidase or peroxidase enzyme.

The matrix material employed in the reagent test strips or devices of this invention are well known in the art and include, by way of illustration, polyethersulfone, fiberglass, polyester, polyethylene, and cellulose-based membranes and the like. Such materials are commercially available from, for example, Gelman Science, Ann Arbor, Mich., USA.

The color change provide by the dry chemistry reagent system of this invention can be read visually or by using conventional instrumentation well known in the art.

By way of example, a dry chemistry reagent indicator dye system is formulated as follows:

Enzyme Solution—Reagent A

The following components are combined and mixed:

30.8 mL water;

55 mL of 1 M citric acid (a buffering agent);

45 mL of 1 M triNA citrate;

20 mL of 50 mg/mL dINA EDTA;

25 mL of 100 mg/mL mannitol in dI water;

53 mL of 100 mg/mL Gantrez S95 in dI water (a color fixing agent consisting of a polyvinyl acid, available from GAF, New York);

300 mL of 250 mg/mL Crotein SPA (a protein stabilizer consisting of hydrolyzed collagens, available from Croda, New York);

100 mL of 11408 units/mL glucose oxidase in dI water;

100 mL of 11880 units/mL peroxidase in dI water.

Dye Solution—Reagent B

The following components are combined and mixed:

480 mL water;

500 mL ethanol;

20 mL of 100 mg/mL SOS in dI water;

6.6 g MBTH-S (sodium salt);

19.8 g ALPS.

Figure 2:
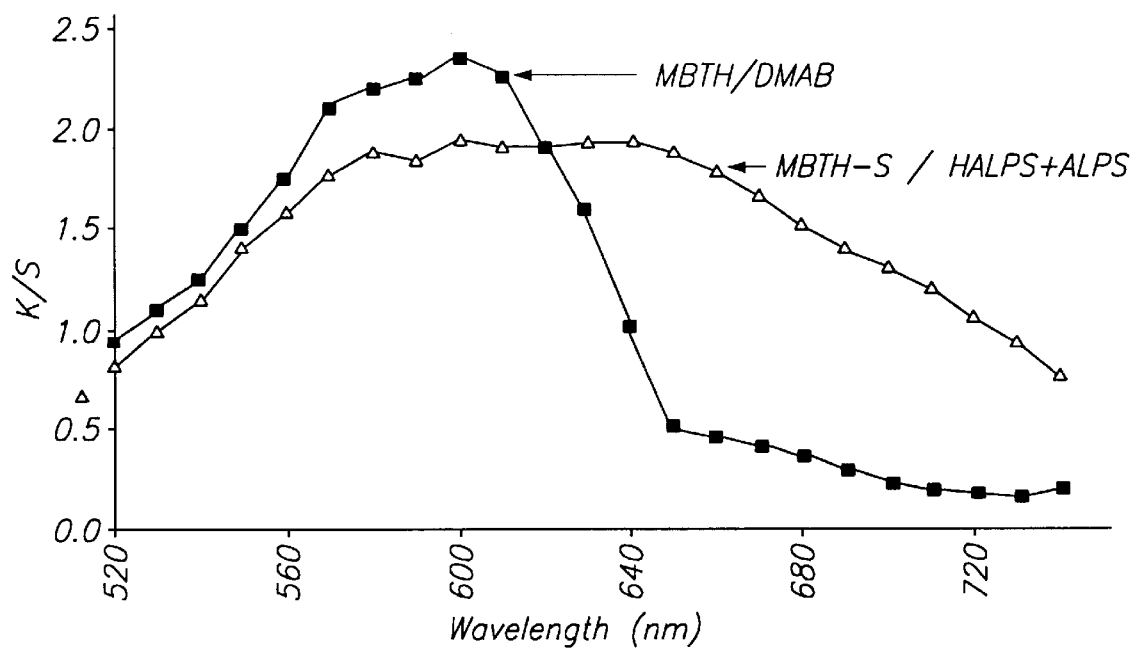
FIG. 2 shows a comparison of the reflectance at certain light wavelengths of dye systems based on (MBTH-S)-ALPS-HALPS and based on MBTH-DMAB

A piece of polyethersulfone membrane from Gelman Science is uniformly coated with Reagent A; the excess is wiped off and the membrane dried. The membrane is then coated with Reagent B in the same fashion and dried. The membrane is then assembled into a test device as shown in FIG. 2 of copending application Ser. No. 08/628,489 (Attorney Docket No. 18176-002) referred to above. Whole blood is applied to the test area and the glucose level is read by visual inspection of the color indication on of the test side of the device. The color changes from clear to a purple to blue color and the fmal color end point forms from clear which is achieved in about 45 seconds and the end point color is calibrated to known concentrations of glucose.

A second formulation was prepared using Reagent C in place of Reagent B.

Dye Solution—Reagent C

The following components are combined and mixed:

480 mL water;

500 mL ethanol;

20 mL of 100 mg/mL SOS in dI water;

6.6 g MBTH-S (sodium salt);

19.4 g HALPS;

396 mg ALPS.

This system provided the same advantages as the Reagent B-based system and had improved dry formulation stability.

FIG. 1 shows the comparative spectral reflective in the range of 520–720 nm for the dye system of the present invention based on a MBTH-S-ALPS dye couple compared to a MBTH-DMAB dye couple, such as disclosed in Kiser U.S. Pat. No. 5,306,623.

FIG. 2 shows the comparative spectral reflective in the range of 520–720 nm for the dye system MBTH-S-HALPS-ALPS for the dye system compared to a MBTH-DMAB dye couple.

Figure 3:
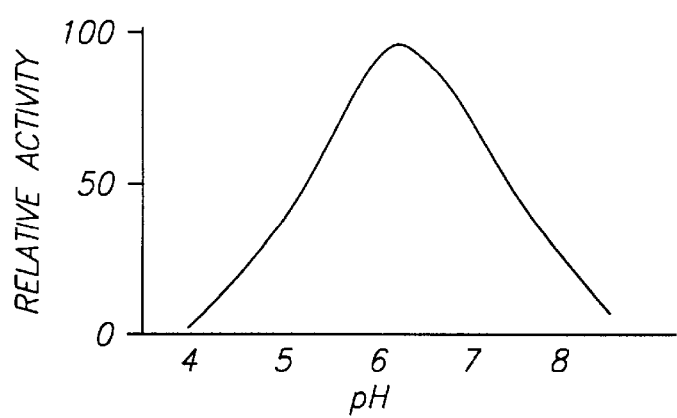
FIG. 3 is an illustration of the relative general activity of enzymes over a pH range.

FIG. 3 is a general illustration of the peroxidase activity of enzymes over a pH range as can be seen it is preferred to have systems which can operate closer to a pH between about 6 and 7. The dye system according to the present invention is stable at a buffered pH of about 6 thus enabling the dye system of this invention to operate in a pH range more favorable to the stability and activity of the oxidase enzymes and peroxidase enzymes present in the dye indicator system.

It will be apparent to one skilled in the art the MBTH-S-based dye indicator of this invention can be formulated in various systems with various oxidase and peroxidase material to provide desired indication of various analytes. It will also be apparent that the systems can be formulated at buffered pH levels which provide a favorable environment for stability of the enzyme components in the dry chemistry reagent system and in the fluid to be analyzed.

What is claimed is:

1. A dry chemistry reagent matrix composition comprising a matrix material and a reagent composition comprising 3-methyl-6(M sulfonate)-benzothiazolinone-(2)-hydrazone (MBTH-S) where M is a positive ion providing a stable sulfonate salt; N-ethyl-N-(3-sulfopropyl)aniline or a salt thereof; and an oxidase enzyme or a peroxidase enzyme or a mixture thereof, wherein the reagent composition is imbibed and dried into or onto the matrix material.

2. The composition according to claim 1 wherein M is a sodium, potassium or ammonium ion.

3. The composition according to claim 1 further comprising a third dye component selected from the group consisting of 3,3-methylaminobenzoic acid, 3,5-dichloro-2-hydroxybenzenesulfonic acid, 8-anilino-1-naphthelenesulfonate, N-(3-sulfopropyl)aniline or salts thereof.

4. The composition according to claim 3 wherein the third dye component is 8-anilino-1-naphthalenesulfonate or a salt thereof.

5. The composition according to claim 3 wherein the third dye component is N-(3-sulfopropyl)aniline or a salt thereof.

6. The composition according to claim 1 wherein the oxidase enzyme is glucose oxidase.

7. The composition according to claim 1 wherein the matrix material is a polyethersulfone.

8. A device for testing a fluid for the presence or concentration of an analyte comprising:

a support member comprising a matrix material;

a dry chemistry reagent composition positioned on or impregnated in said support member, said reagent composition comprising 3-methyl-6(M sulfonate)-benzothiazolinone-(2)-hydrazone (MBTH-S) where M is a positive ion providing a stable sulfonate salt; N-ethyl-N-(3-sulfopropyl)aniline or a salt thereof; and an oxidase enzyme or a peroxidase enzyme or a mixture thereof;

whereby the support member is adapted for receiving a fluid sample which contacts said composition and adapted for the support member to provide for inspection or reading of the color change produced by said reagent composition after contact with the fluid sample.

9. The device according to claim 8 wherein M is a sodium, potassium or ammonium ion.

10. The device according to claim 8 wherein the dry chemistry reagent system further comprises a third dye component selected from the group consisting of 3,3-dimethylaminobenzoic acid, 3,5-dichloro-2-hydroxybenzenesulfonic acid, 8-anilino-1-naphthelenesulfonate, N-(3-sulfopropyl)aniline or salts thereof.

11. The device according to claim 10 wherein the third dye component is 8-anilino-1-naphthalenesulfonate or a salt thereof.

12. The device according to claim 10 wherein the third dye component is N-(3-sulfopropyl)aniline or a salt thereof.

13. The device according to claim 8 wherein the oxidase enzyme is glucose oxidase.

14. The device according to claim 8 wherein the matrix material is a polyethersulfone.

15. A method of testing a fluid for the presence or concentration of an analyte comprising:

applying a fluid sample to a support member comprising a matrix material having positioned thereon or impregnated therein a dry chemistry reagent composition comprising 3-methyl-6-(M sulfonate)-benzothiazolinone-(2)hydrazone (MBTH-S) where M is a positive ion providing a stable sulfonate salt; N-ethyl-N-(3-sulfopropyl)aniline or a salt thereof; and an oxidase enzyme or a peroxidase enzyme or a mixture thereof; whereby the support member is adapted for receiving a fluid sample which contacts said reagent composition and adapted for the support member to provide for inspection or reading of the color change produced by said reagent composition after contact with the fluid sample; and reading or measuring the color indication provided by said reagent composition after contact with said fluid sample.

16. The method according to claim 15 wherein M is a sodium, potassium or ammonium ion.

17. The method according to claim 15 wherein the dry chemistry reagent system further comprises a third dye component selected from the group consisting of 3,3-dimethylaminobenzoic acid, 3,5-dichloro-2-hydroxybenzenesulfonic acid, 8-anilino-1-naphthelenesulfonate, N-(3-sulfopropyl)aniline or salts thereof.

18. The method according to claim 17 wherein the third dye component is 8-anilino-1-naphthalenesulfonate or a salt thereof.

19. The method according to claim 17 wherein the third dye component is N-(3-sulfopropyl)aniline or a salt thereof.

20. The method according to claim 15 wherein the oxidase enzyme is glucose oxidase.

21. The method according to claim 15 wherein the matrix material is a polyethersulfone.

* * * * *